United States Patent [19]

Fumoto

[11] Patent Number: 4,510,389

[45] Date of Patent: Apr. 9, 1985

[54] INFRARED FILM THICKNESS GAGE

[75] Inventor: Takabumi Fumoto, Kanagawa, Japan

[73] Assignees: Fuji Electric Company, Ltd.; Fuji Electric Corporate Research and Development, Ltd., both of Japan

[21] Appl. No.: 421,323

[22] Filed: Sep. 22, 1982

[30] Foreign Application Priority Data

Oct. 17, 1981 [JP] Japan ............................... 56-153463

[51] Int. Cl.³ .............................................. G01N 21/35
[52] U.S. Cl. ................................... 250/339; 250/358.1
[58] Field of Search .................. 250/339, 493.1, 495.1, 250/341, 360.1, 359.1, 358.1; 361/266

[56] References Cited

U.S. PATENT DOCUMENTS

| | | | |
|---|---|---|---|
| 3,372,305 | 3/1968 | Mikulec | 219/267 |
| 3,536,919 | 10/1970 | Newman | 250/493.1 |
| 4,243,882 | 1/1981 | Yasujima et al. | 250/339 |
| 4,429,225 | 1/1984 | Fumoto et al. | 250/353 |

OTHER PUBLICATIONS

J. J. Howarth and H. M. Stanier, "An Infra-Red Process Analyser Based on Interference Filters", *J. Sci. Instrum.*, vol. 42, (1965), pp. 526–528.

*Primary Examiner*—Janice A. Howell
*Assistant Examiner*—Constantine Hannaher
*Attorney, Agent, or Firm*—Brumbaugh, Graves, Donohue & Raymond

[57] ABSTRACT

An infrared film thickness gage for continuous on-line thickness measurement of a plastic film produced by a film blowing process into a tube shape has an infrared source with generally uniform directional radiation characteristics and is concentrically positioned inside the film tube. A photodetector is positioned outside the film tube in confronting relation to the source and receives the infrared rays of different reference and measurement wavelengths after the infrared rays have passed through the tube. Converting means receives the output of the photodetector, and since the film has different known attenuation coefficients for the different wavelengths, the thickness of the film can be determined. By using an infrared source having uniform directional characteristics and a filter to filter out instantaneous background light, measurement errors are substantially reduced or eliminated.

9 Claims, 30 Drawing Figures

INFRARED FILM THICKNESS GAGE

TECHNICAL FIELD

The present invention relates principally to an infrared film thickness gage capable of continuous on-line thickness measurement of plastic film during production by a film blowing process. The present invention also relates to an infrared film thickness gage capable of continuously measuring the thickness of a transparent or translucent polymer film with high precision, and more particularly to an improved infrared film thickness gage which is substantially free of measurement errors otherwise caused by external light such as room illumination light or sunlight falling upon a measuring unit during film thickness measurement.

BACKGROUND OF THE INVENTION

Polymer films as of polyethylene or nylon, particularly those having an extremely small thickness of 50μ or less, are generally factory-produced continuously at high speeds. It is highly important for product quality control and material savings that the thickness of the film as it is manufactured be measured and monitored to see if it meets required specifications. Film thickness measurements have conventionally been carried out by β-ray film thickness gages of the contactless type. However, since the β-ray film thickness gages use a radioisotope as the source of β-ray radiation, they are dangerous to handle. Furthermore, a radiation shield, which happens to be quite expensive, must be installed for protection, and under some existing laws a chief radiation technician must operate or monitor the gage. Therefore βray film thickness gages have been employed on only a limited basis.

As an alternative to the β-ray film thickness gages, contactless-type infrared film thickness gages which rely on infrared radiation as a measuring medium have been employed. Infrared film thickness gages operate on the principle that infrared radiation has different attenuation coefficients for different wavelength bands for a film irradiated by the infrared radiation. More specifically, a test film is irradiated alternately with an infrared ray having a wavelength λR (hereinafter referred to as the "reference wavelength") which has a smaller attenuation coefficient, and an infrared ray having a wavelength λM (hereinafter referred to as the "measurement wavelength") which has a larger attenuation coefficient. A light detector detects the intensity of light after it has been transmitted through the film, and the detected light intensity for the two wavelengths is converted into a common logarithm ratio to calculate the thickness of the film. However, due to sudden changes in the amount of background light caused by energizing a fluorescent light or opening a window shade or blind, measurement errors occur. These measurement errors often exceed the acceptable tolerance level required for measurements of this type. Therefore, an acceptable measuring device having the necessary accuracy even when subjected to background sources is needed.

As mentioned above, the present invention relates principally to an infrared film thickness gage capable of continuous on-line measurement of the thickness of plastic film being produced by a film blowing process (also known as an inflation method).

Film blowing for forming plastic film is generally carried out by an extruder which melts and compresses resin material and extrudes the melted mass through a ring die having an annular gap to form a plastic film into a tubular form. The ring die has an air blowing pipe for introducing air into the interior of the tube to inflate the tube.

For making the quality or thickness of the film more uniform, the apparatus for forming plastic film measures the thickness at various parts of the film at a position where the plastic film is inflated into the tubular form, and adjusts the gap in the ring die to keep the film thickness uniform.

Thickness gages for measuring the thickness of an inflated film tube must measure films having a thickness ranging from about 0 to 300μ, at a precision of ±1μ. To meet these requirements, an infrared film thickness has been employed to measure the thickness of inflated film tubes. The infrared film thickness gage operates on the principle that infrared radiation has different attenuation coefficients for different wavelength bands for a film irradiated by the infrared radiation. More specifically, a test film is irradiated alternately with an infrared ray having reference wavelength λR which has a smaller attenuation coefficient, and an infrared ray having a wavelength λM which has a greater attenuation coefficient. A light detector detects the intensity of light after it has been transmitted through the film and the detected light intensity for the two wavelengths is converted into a common logarithm ratio to calculate the thickness of the film.

When measuring the thickness of film made during the inflation process the interior of the inflated tube tends to be heated up to a temperature of about 200 degrees Celsius. Therefore, a light source including a filter and motor and installed inside of the film tube is exposed to extreme heat and has a relatively short service life and poor operation stability. In an attempt to overcome these problems a conventional infrared film thickness gage arrangement has been used wherein only the source of infrared radiation is positioned within the film tube. The photodetector is installed outside of the film tube to pick up infrared rays of the measurement and reference wavelengths.

In such an arrangement, a tungsten-filament lamp has been used as the source of infrared radiation. However, since the direction distribution of radiation intensity of a tungsten lamp is not uniform, upon scanning the zero point shifts as will be explained.

Infrared detectors are based on the principle that the resistance of a photosensitive element varies in proportion to light intensity to detect an infrared ray. The infrared detectors have resistance vs. light intensity characteristics which are different for different wavelengths. While the resistance vs. light intensity characteristics of the infrared detectors have a relatively rectilinear relationship for various wavelengths in a region in which the light intensity is small, the characteristics become nonlinear as the light intensity increases, and differ from each other with the wavelengths. Where the directional distribution of radiation intensity of the infrared radiation source is nonuniform as described above, the zero point shifts by an amount of about 1μ to 1.5μ in a scanning operation. Thickness gages using tungsten-filament lamps have an accuracy far less than 1μ, a level required by thickness gages for inflated tubular films. Therefore, such thickness gages are useless for measuring films made during the inflation process.

SUMMARY OF THE INVENTION

It is an object of the present invention to provide a precision infrared film thickness gage which will be substantially free of thickness measurement errors even under conditions where the intensity of room illumination light or sunlight coming into a room is instantaneously increased or reduced.

According to the present invention, the above object is achieved by an infrared film thickness gage having a light source for radiating infrared rays having a reference wavelength and a measurement wavelength alternately upon a test film, and a photodetector for receiving the infrared rays after transmission through the test film and means for converting an intensity of the received infrared rays into an electrical signal. The photodetector has in its optical path an infrared longpass filter having a cutoff wavelength in the vicinity of the reference and measurement wavelengths. The infrared long-pass filter has an infrared transmittance which is held at maximum in the vicinity of peaks of the reference and measurement wavelenghts.

The infrared ray detector preferably comprises a photoconductive detector having a thin photosensitive film of lead sulfide, and the infrared long-pass filter preferably has a cutoff wavelength $\lambda c$ of $1.7\mu$ or $1.4\mu$.

It is a major object of the present invention to provide an infrared film thickness gage capable of measuring the thickness of inflated film tubes with high precision while reducing measurement errors upon scanning by a photodetector.

The present inventor has made studies in an effort to alleviate the infrared film thickness gage of the prior art used for measuring the thickness of inflated film tubes. The inventor has found that radiation intensity distribution can be rendered uniform by using an infrared radiation source comprising a rod-shaped heater assembly including a pipe of ceramic material and a flat or sheet-shaped heater wound around the pipe. Such a radiation source can prevent the zero point from shifting during a scanning operation of the photodetector.

According to the present invention, the above object can be achieved by an infrared film thickness gage having a source of infrared radiation for irradiating a test film with infrared rays, and a photodetector for receiving the infrared rays of reference and measurement wavelengths after having passed through the test film alternately, and means for converting an intensity of the received infrared rays into an electrical signal. The source of infrared radiation has uniform directional distribution characteristics of radiation intensity and is concentrically disposed in a film tube. The photodetector is disposed outside of the film tube in confronting relation to the source of infrared radiation.

The infrared radiation source preferably comprises a rod-shaped heater or helical-shaped SiC heater including a pipe of ceramic material and a flat or sheet-shaped heater wound circumferentially around the pipe.

Numerous other advantages and features of the present invention will become readily apparent from the following detailed description of the invention and of one embodiment thereof, from the claims and from the accompanying drawings.

BRIEF DESCRIPTION OF THE DRAWINGS

FIGS. 18 (a)–(c) show patterns of directional distribution characteristics of radiation intensity of the infrared radiation sources of the invention and a prior infrared radiation source;

FIGS. 25 (a)–(d) are graphs showing occurences of zero point shifting obtained from scanning with an infrared radiation source according to the invention and with the infrared radiation sources as shown in FIGS. 22 through 24.

DETAILED DESCRIPTION OF THE PREFERRED EMBODIMENT

The present invention relates to an improvement in an infrared film thickness gage. For a fuller understanding of the present invention described later, the fundamental structure and operation principles of a typical infrared film thickness gage will first be described with reference to FIG. 1.

Figure 1:
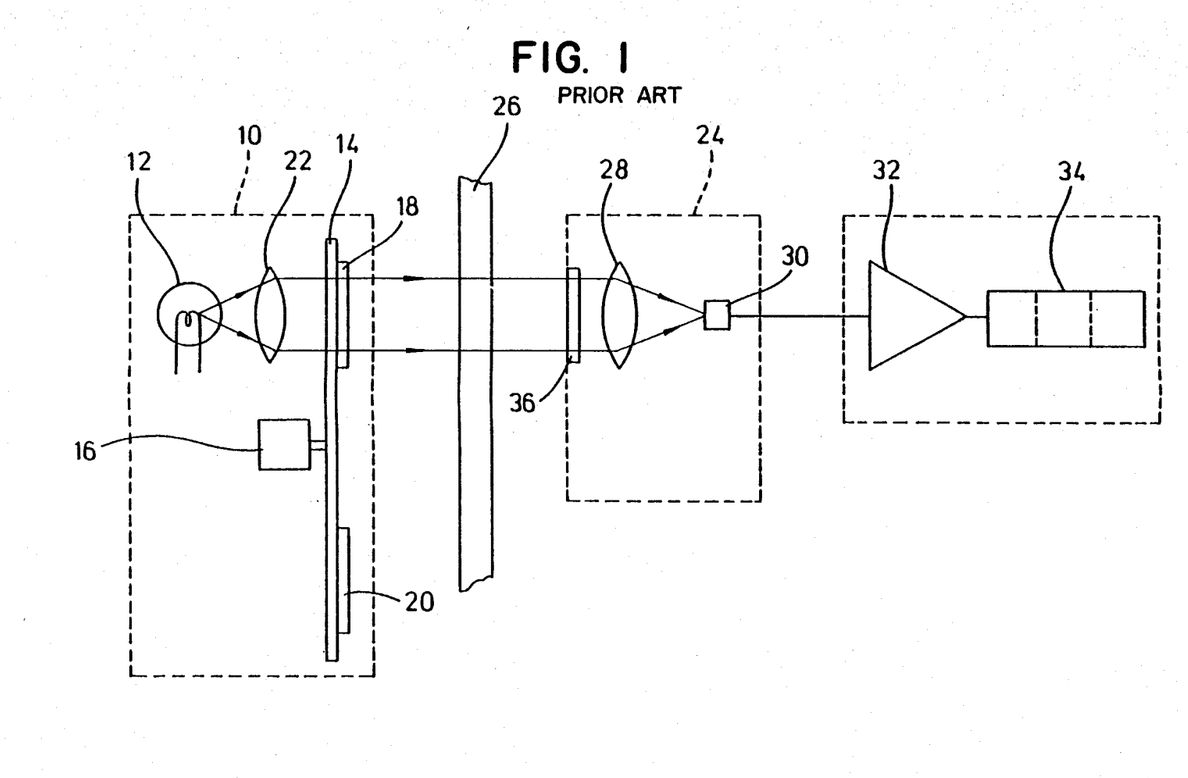
FIG. 1 is a schematic view of a conventional infrared film thickness gage.

As shown in FIG. 1, the thickness gage includes a light source 10 for radiating infrared rays. The light source 10 comprises an infrared source 12 such as a tungsten-filament lamp or a Globar lamp, and a chopper composed of a rotatable disc 14 and an synchronous motor 16 for driving the rotatable disc 14. The rotatable disc 14 has a pair of diametrically opposite through holes across a shaft of the motor 16. The disc 14 has at its holes a bandpass filter 18 for transmitting therethrough only the infrared radiation having the reference wavelength R, and a bandpass filter 20 for transmitting therethrough only the infrared radiation having the measurement wavelength M. Between the infrared souce 12 and the rotatable disc 14, there is provided a lens 22 in alignment with the filter 18 or 20.

The infrared rays which are emitted from the infrared source 12 become parallel as they pass through the lens 22, and are chopped by the bandpass filters 18, 20 upon rotation of the disc 14. Thus, the infrared rays having the reference and measurement wavelengths $\lambda R$, $\lambda M$ alternately irradiate a film (described below).

A photodetector 24 is located at a distance from the light source 10. A film 26 to be measured for thickness is interposed between the light source 10 and the photodetector 24 so as to be longitudinally fed continuously. The photodetector 24 includes a condenser lens 28 having an optical axis which is in alignment with that of the lens 22. The photodetector 24 also has an infrared detector 30 which comprises a photoconductive cell of lead sulfide or lead selenide and which is positioned at a focal point of the condenser lens 28. The infrared detector 30 is connected to an arithmetic electronic circuit 32 that is coupled to a digital display 34 numerically indicating the thickness of the film being measured.

In operation, the infrared rays of the reference wavelength $\lambda R$ and the measurement wavelength $\lambda M$ are chopped by the bandpass filters 18, 20 and alternately fall upon the test film 26. The infrared rays, after they have passed through the filters 18, 20, are detected by the infrared detector 30 which converts the infrared rays into electrical signals that are in proportion to the intensities of the infrared rays of the reference and measurement wavelengths. The electrical signals are then inputted to the arithmetic electronic circuit 32 and converted into a logarithmic ratio. Thereafter, the thickness of the film 26 is digitally displayed on the display 34.

The infrared film thickness gage thus constructed can make simple and safe measurements of the thicknesses of films that are being continuously produced on a production line. The conventional infrared film thickness gage has however proven unsatisfactory in that the infrared detector is subjected to external light such as room illumination light at the place of measurement or sunlight coming through the window into the room, resulting in errors in film thickness measurements. To provide against such disturbances due to external visible light, a visible-light cutoff filter 36 has been used in front of the condenser lens 28 in the photodetector 24, as shown in FIG. 1. The visible rays of light generally have a wavelength ranging from 0.78 to 0.38$\mu$. Visible light such as room illumination light or sunlight can therefore be cut off by a filter having a transmission characteristic as shown by the curve A in FIG. 2. Thus, adverse effects due to such visible light can be eliminated by such an additional filter. With the visible-light cutoff filter, however, it has been found that when a fluorescent lamp in the room is turned on or off, or the window blind is opened or closed to adjust light admission, the zero point shifts by an amount of about 1$\mu$ to 1.5$\mu$, with a resulting error in thickness measurement.

Figure 3:
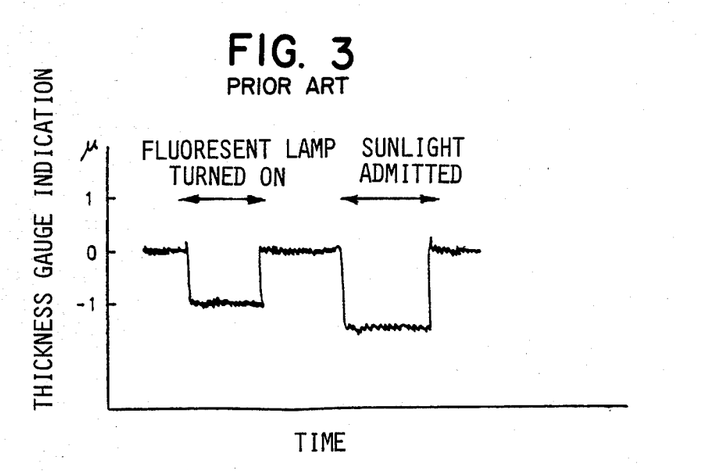
FIG. 3 is a graph illustrating the shifting of the zero point of the infrared film thickness gage shown in FIG. 1 when the intensity of external light changes.

The present applicant is an inventor in U.S. Pat. No. 4,429,225 entitled "Infrared Thickness Measuring Device" for reducing measurement errors due to optical interference by irradiating a test film with scattered infrared rays for thickness measurement of a thin film that is 50$\mu$ or less thick. Such a thickness gage also includes a visible-light cutoff filter disposed in a light admission hole in a photodetector or at the bottom of a conical light concentration guide. However, the thickness gage still undergoes measurement errors at the time of turn-on or turn-off of the fluorescent lamp or closing or opening of the window blind. A result of measurement made by the thickness gage is illustrated in FIG. 3. A study of FIG. 3 indicates that the zero point is shifted by an amount of about 1$\mu$ to 1.5$\mu$ when the fluorescent lamp is energized or the window blind is opened.

Such a measurement error is caused by a variation in the intensity of incident light due to turn-on of the fluorescent lamp or opening of the window blind. The intensity variation is attributable to the shifting of the zero point for the reasons described below. The present inventor has found that such a difficulty can be overcome by an infrared long-pass filter having a transmission characteristic as shown by the curve B in FIG. 2.

The present invention will now be described with reference to the drawings in which preferred embodiments of infrared film thickness gages are shown. The reasons why an infrared long-pass filter can avoid adverse effects due to variations in intensity of external light will also be discussed.

Figure 2:
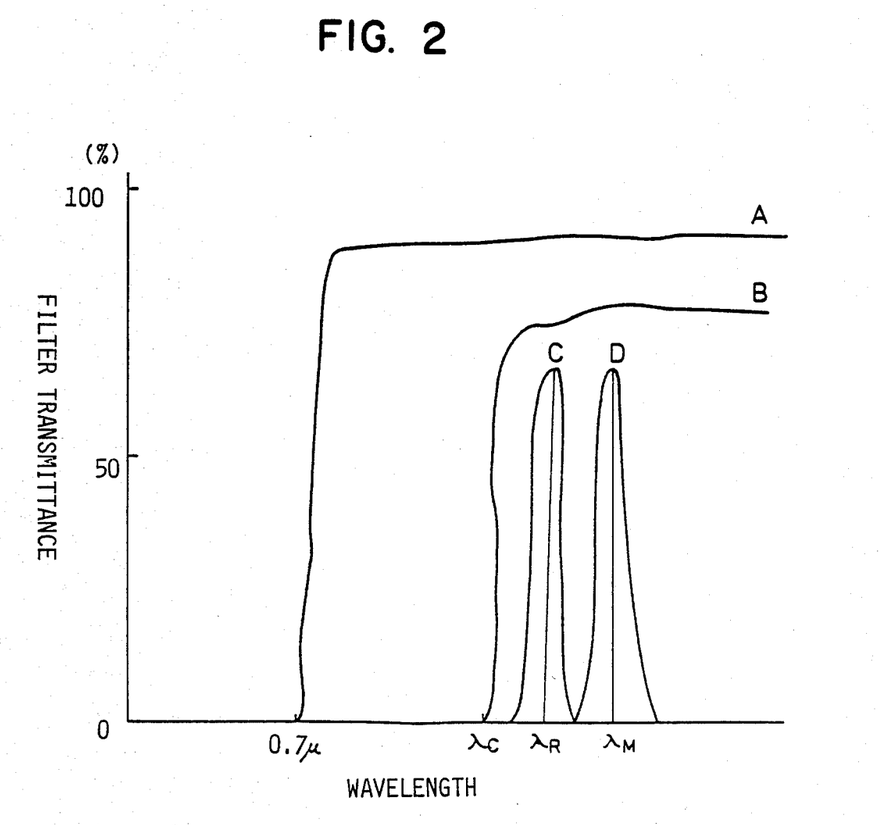
FIG. 2 is a graph showing infrared filter transmittances for various wavelengths.
Figure 4:
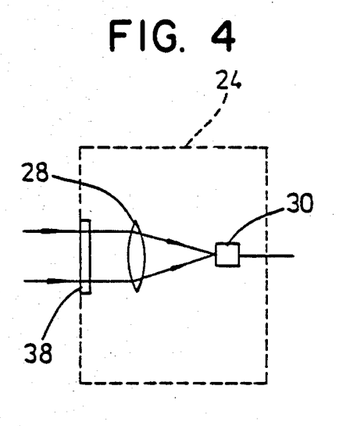
FIGS. 4 through 7 are schematic views of infrared film thickness gages according to embodiments of the present invention.

FIGS. 4 through 7 show preferred embodiments of the present invention. As shown in FIG. 4, an infrared film thickness gage includes a photodetector 24, similar to that shown in FIG. 1, having an infrared-ray admission hole which confronts a light source (not shown). The photodetector 24 includes an infrared long-pass filter 38 disposed in such an infrared-ray admission hole. As illustrated at B in FIG. 2, the infrared long-pass filter 38 has a cutoff wavelength $\lambda c$ that is as close to the reference and measurement wavelengths $\lambda R$, $\lambda M$ as possible, and also has a transmittance which is largest in the vicinity of peaks C, D of the reference and measurement wavelengths $\lambda R$, $\lambda M$. For example, where the reference wavelength $\lambda R$ is 20$\mu$ (half-width: 200 nm), and the measurement wavelength $\lambda M$ is 240$\mu$ (half-width: 200 nm), the infrared long-pass filter should preferably have a cutoff wavelength $\lambda c$ of 1.7$\mu$. The infrared long-pass filter 38 having such characteristics can cut off external light such as room illumination light or sunlight having a wavelength band ranging from 0.7$\mu$ to the cutoff wavelength $\lambda c$ as shown in FIG. 2, from falling upon the photodetector 24. Therefore, the long-pass filter 38 practically prevents shifting of the zero point due to light intensity variations that are caused when the fluorescent lamp in the room is turned on or the window blind is opened.

Figure 5:
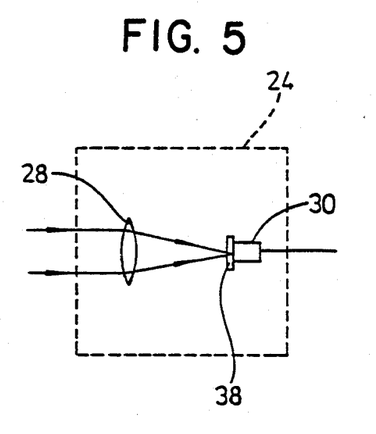
Figure 6:
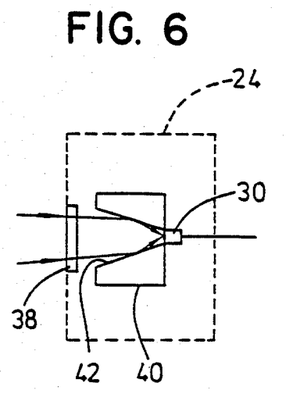

FIG. 5 shows a photodetector 24 which is of the same construction as that of the photodetector 24 shown in FIG. 4, except that an infrared long-pass filter 38 is disposed just in front of an infrared detector 30. FIG. 6 illustrates a photodetector of an infrared film thickness gage (as disclosed in Japanese patent application No. 55-177184) according to another invention, which is suitable for measuring a very thin film having a thickness of 50$\mu$ or less. The photodetector has an infrared long-pass filter 38. The photodetector also includes a light concentration guide 40 having a conical reflective surface 42.

Figure 7:
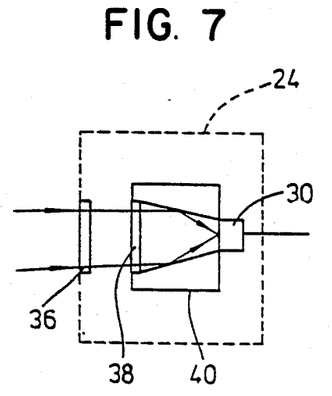

FIG. 7 is illustrative of a modification of the arrangement shown in FIG. 6. An infrared long-pass filter 38 is located in a light admission opening of a conical reflective surface 42 of a light concentration guide 40 in a photodetector 24. A visible-light cutoff filter 36 is also located in the photodetector 24 at its light admission hole. Therefore, adverse effects due to admission of external light can be prevented by the two filters 36, 38.

As with the photodetector shown in FIG. 4, the photodetectors illustrated in FIGS. 5 through 7 can effectively cut off external incident light having wavelengths ranging from $0.7\mu$ to the cutoff wavelength $\lambda c$, thus lowering measurement errors due to such unwanted external light.

The reasons why the infrared long-pass filter can eliminate influences of external light will be described in detail by referring to characteristics of the infrared detector. The infrared detector used as a means for detecting infrared radiation in the infrared film thickness gage comprises a photoconductive detector having a photosensitive surface in the form of a polycrystalline film of lead sulfide or lead selenide for detecting a change in electrical resistance caused by a change in the intensity of light falling upon the photosensitive surface. The change in electrical resistance is proportional to the change in the intensity of incident light.

Figure 8:
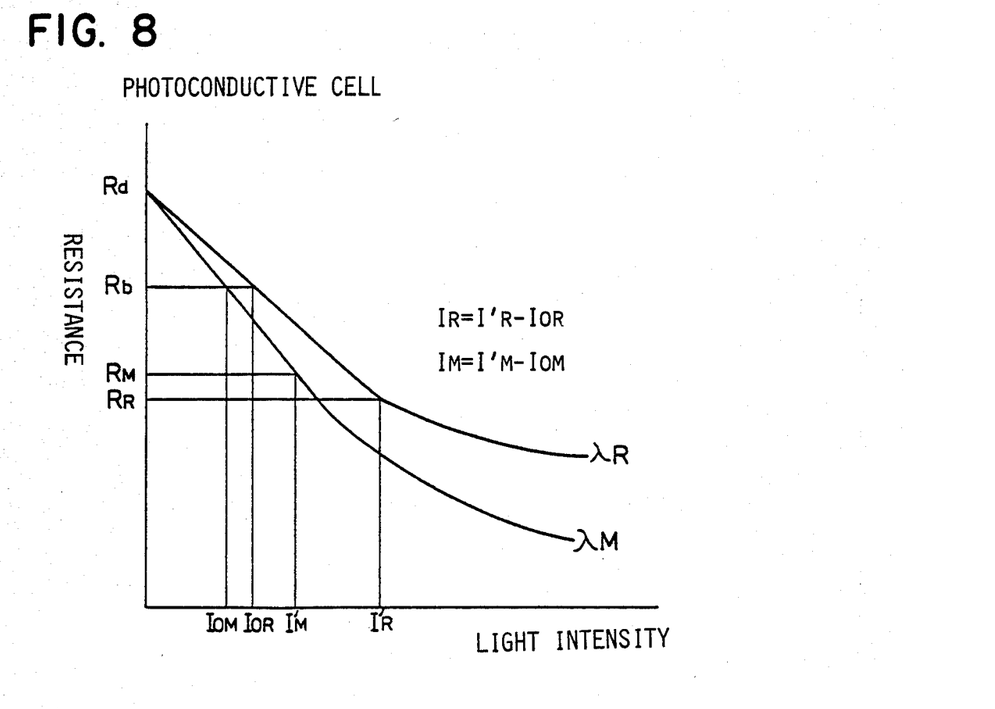
FIG. 8 is a graph showing resistance variations with respect to intensities of light falling upon a photoconductive infrared detector.

The photoconductive infrared detector has resistance vs. light intensity characteristics as shown in FIG. 8. The characteristics vary with different wavelengths of infrared radiation falling on the infrared detector. More specifically, the resistance changes substantially rectilinearly for both the wavelengths $\lambda R$, $\lambda M$ in the range in which the light intensity is not sufficiently large. As the intensity of incident light increases, the resistances vary differently for the wavelengths. Designated in FIG. 8 at Rd is a dark resistance with no light falling upon the infrared detector, Rb a background resistance with external light falling upon the infrared detector, and $R_R$, $R_M$ resistances detected when the infrared rays (hereinafter referred to as "signal light") of the wavelengths $\lambda R$, $\lambda M$ and the external light fall upon the infrared detector. Also indicated at $I_{OR}$, $I_{OM}$ are light intensities indicative of resistance variations as converted according to the characteristics of the reference and measurement wavelengths $\lambda R$, $\lambda M$, the resistance variations taking place when external light having a wide wavelength band falls upon the infrared detector, and at $I'R$, $I'M$ light intensities corresponding to the resistances detected when the external light and signal light fall upon the infrared detector. Therefore, the intensity $I_R$ of signal light at the wavelength $\lambda R$ can be given by $I'R - I_{OR}$, and a resistance variation $\Delta R_R$ corresponding to $I_R$ can be given by $R_R - Rb$. The intensity $I_M$ of signal light at the measurement wavelength $\lambda M$ can be determined by $I'M - I_{OM}$, and a resistance variation $\Delta R_M$ corresponding to $I_M$ can be determined by $R_M - Rb$.

Figure 9:
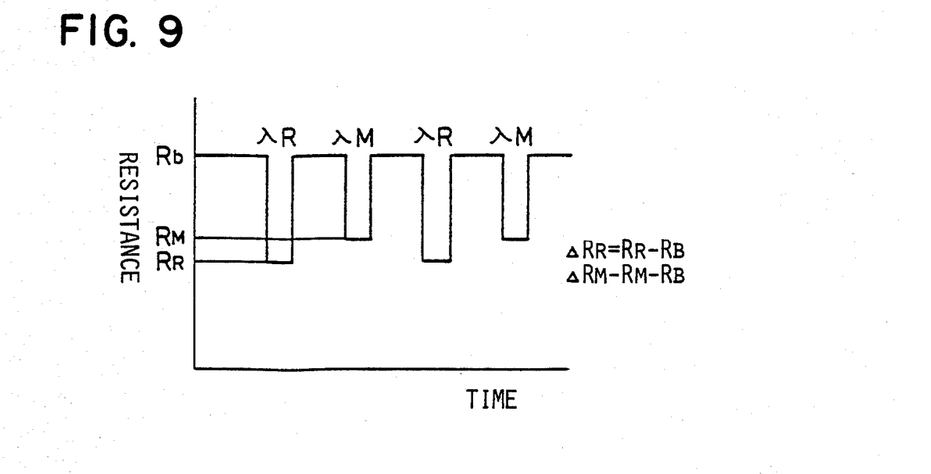
FIG. 9 is a graph showing the waveform of an output of an infrared detector.

FIG. 9 shows the waveform of an output of the infrared detector 30 in the conventional infrared film thickness gage, the waveform being shown in the form of resistances (y-axis) that vary with time (x-axis). The output is electrically processed to subtract the background resistance Rb, so that electrical signals which are proportional to $\Delta R_R = R_R - Rb$ and $\Delta R_M = R_M - Rb$ can be detected.

According to Lambert-Beer's law, the following relationship can be established:

$$\ln(I_R(d)/I_M(d)) = \ln(I_R(o)/I_M(o)) + Cd$$

where $I_R(d)$, $I_M(d)$ are the intensities of infrared rays of the wavelengths $\lambda R$, $\lambda M$ which are passed through a film having a thickness of d, $I_R(o)$, $I_M(o)$ are the intensities of such infrared rays having passed through no film, and C is a constant. When the light intensities are proportional to the resistance variations in the detector, then the following relationship can be established:

$$d = C'((\ln(R_R(d)/R_M(d)) - \ln(R_R(o)/R_M(o)))$$

where $\Delta R_R(d)$, $\Delta R_M(d)$, $\Delta R_R(o)$, $\Delta R_M(o)$ are resistance variations corresponding to $I_M(d)$, $I_M(d)$, $I_R(o)$, $I_M(o)$, respectively, and $C'$ is a constant. The ratio $I_R(o)/I_M(o)$ is a constant which is determined by the temperature of a source of infrared radiation, and hence the ratio $\Delta R_R(o)/\Delta R_M(o)$ is constant. An output which is in proportion to the film thickness d can thus be picked up by subtracting the constant $R_R(o)/R_M(o)$ from the measured value $\ln(R_R(d)/R_M(d))$.

Where the intensity of the external light is not sufficiently large and $R_M$, $R_R$ are in the rectilinear region as shown in FIG. 8, $\Delta R_R(o)/\Delta R_M(o)$ remains unchanged when the external light varies unless the intensity of infrared rays for measurement is changed, and hence the zero point remains where it is. When the external light intensity is increased to the extent that $R_M$, $R_R$ as shown in FIG. 8 are displaced from the rectilinear region into the curved region, $\Delta R_R(o)/\Delta R_M(o)$ varies with the intensity of the external light even if $I_R(o)/I_M(o)$ are constant, since the intensity vs. resistance variation characteristics are different for the reference and measurement wavelengths $\lambda R$, $\lambda M$, and hence the zero point shifts. Therefore, it is necessary that the intensity of the external incident light be as small as possible, and $R_R$, $R_M$ as illustrated in FIG. 8 be maintained within the rectilinear region. With the conventional visible filter, however, external light having a waveform band ranging from $0.7\mu$ to $\lambda c$ is allowed to enter the detector, as shown in FIG. 2, and $R_R$, $R_M$ in FIG. 8 are shifted into the curved region, so that the zero point shifts when the fluorescent lamp in the room is turned on or the window blind is opened to thereby cause the external light intensity to change.

With the infrared long-pass filter having characteristics as shown by the curve in FIG. 2 being used according to the embodiments illustrated in FIGS. 4 through 7, external light having wavelengths below $\lambda c$ is prevented from entering the infrared detector 30. The resistances $R_R$, $R_M$ are confined in the rectilinear region as shown in FIG. 8, and hence the zero point will not be shifted when the external light changes in intensity.

Figure 10:
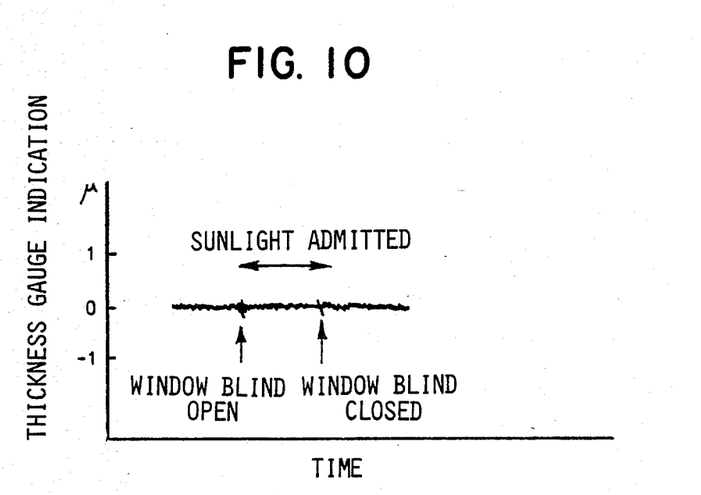
FIG. 10 is a graph illustrating the shifting of the zero point of an infrared film thickness gage of the invention when the intensity of external light varies.

A result of measurement made by the arrangement of FIG. 7 is shown in FIG. 10. When a prior infrared film thickness gage is used for measurements, the zero point shifts by an amount of about $1\mu$ to $1.5\mu$ as shown in FIG. 3 when the fluorescent lamp in the room is turned on or off or the window blind is opened or closed. With the present invention, however, practically no shift in the zero point will result as illustrated in FIG. 10.

Figure 11:
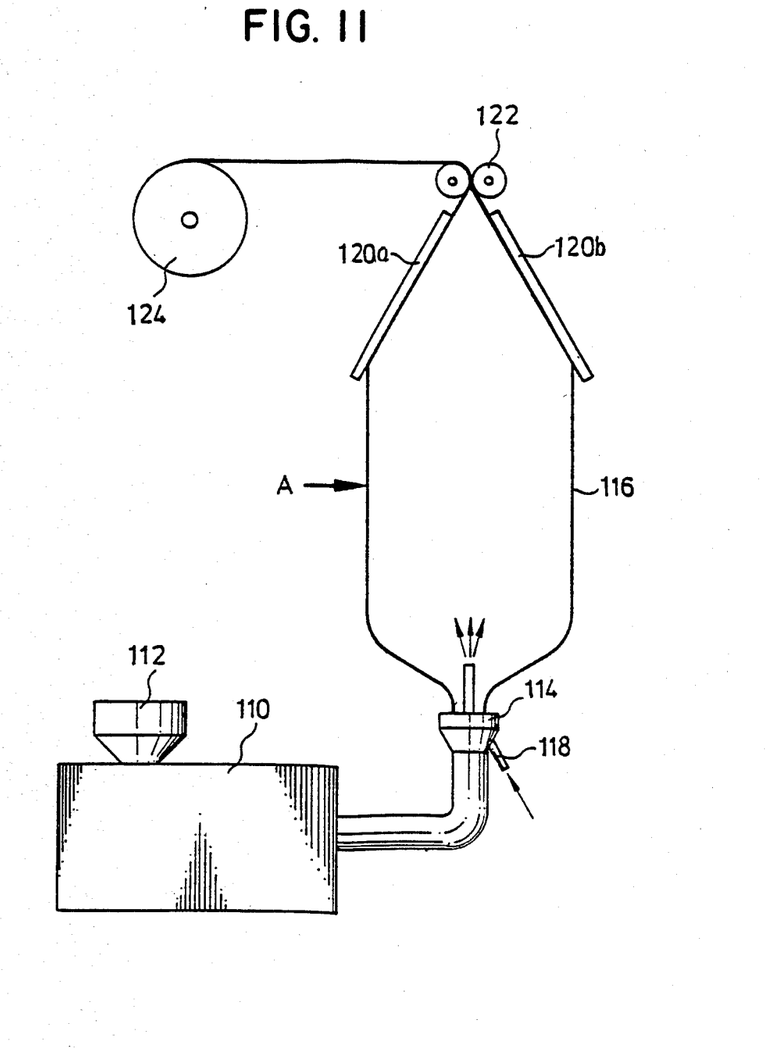
FIG. 11 is a schematic view illustrating the principle of forming a tubular film using a film blowing process.

As mentioned above, the present invention relates principally to an infrared film thickness gage capable of continuous on-line thickness measurement of plastic film being produced by a film blowing process or inflation method. Film blowing for forming plastic film is generally carried out on the principle illustrated in FIG. 11. As shown in FIG. 11, an extruder 110 is supplied with a grainy resin material through a resin inlet 112, melts and compresses the resin material, and extrudes the melted mass through a ring die 114 having an annular gap into a plastic film 116. The ring die 114 has an air blowing pipe 118 attached thereto for introducing air into the interior of the plastic film 116 as it is formed continuously into a tubular form to inflate the plastic film into a tube. The plastic film 116 thus formed is guided by receiver plates 120a, 120b, collapsed by a pair of pinch rolls 122, and finally wound on a takeup roll 124.

For making the quality or thickness of the film more uniform, the apparatus for forming plastic film measures the thickness at various parts of the film at a position A where the plastic film 116 is inflated into the tubular form, and adjusts the gap in the ring die 114 to keep the film thickness uniform.

Figure 12:
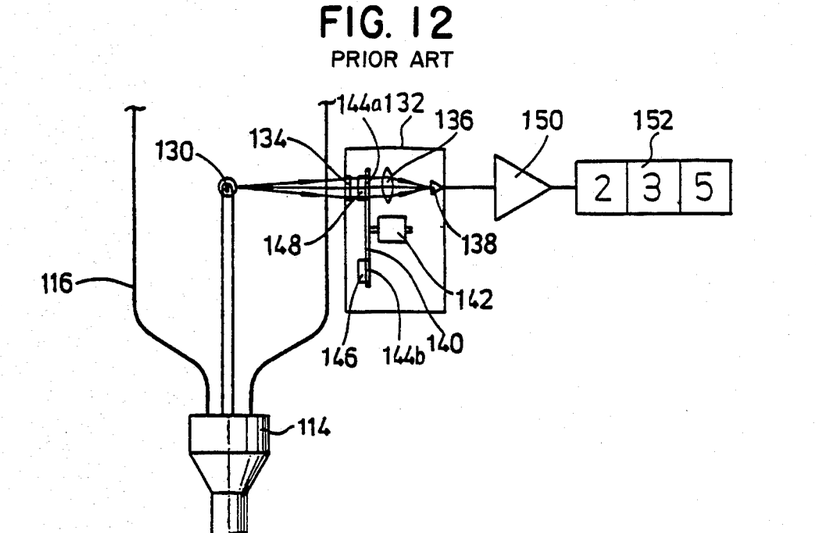
FIG. 12 is a schematic view of a conventional infrared film thickness gage.

More specifically, as illustrated in FIG. 12, a source 130 of infrared radiation comprises a tungsten-filament lamp disposed within the film tube 16. A photodetector 132 is located outside of the film tube 116 in confronting relation to the infrared radiation source 130. The photodetector 132 has an infrared radiation transmission window 134 facing the infrared radiation source 130, and also includes therein a lens 136, an infrared detector 138 of PbS, PbSe or the like, and a chopper composed of a rotatable disc 140 and a synchronous motor 142 for driving the rotatable disc 140. The rotatable disc 140 has a pair of diametrically opposed through-holes 144a, 144b, across a shaft of the synchronous motor 142. A bandpass filter 146, having a range which allows the infrared ray of the wavelength $\lambda R$ to pass therethrough, is attached at one of the holes 144, and another bandpass filter 148 having a range which allows the infrared ray of the wavelength of $\lambda M$ to pass therethrough is attached at the other hole 144. The infrared radiation source 130, the infrared radiation transmission window 134, the filters 146, 148, and the infrared detector 138 are required to be positioned in alignment with an optical axis of the lens 136. The infrared detector 138 in the photodetector 132 is electrically connected to an arithmetic unit 150, which is coupled to a display 152 for indicating film thicknesses as measured.

Figure 13:
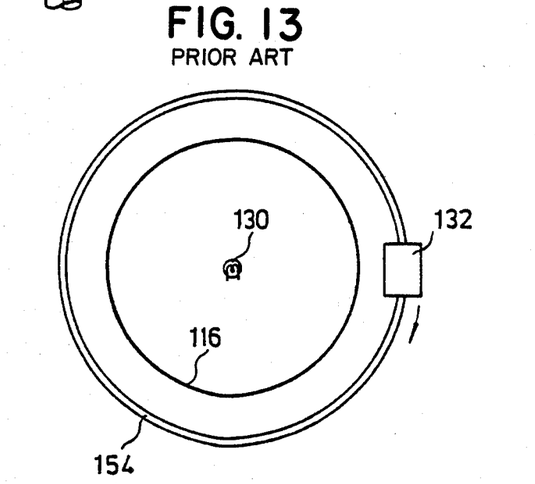
FIG. 13 is a view showing a photodetector in the thickness gages of FIG. 12, as positioned with respect to a test material.

In operation, infrared rays emitted from the infrared source 130 pass through a test film 116 and enter the photodetector 132. The infrared rays are chopped by the bandpass filters 146, 148 to permit the transmitted infrared rays of the reference and measurement wavelengths $\lambda R$, $\lambda M$ alternately to pass through the lens 136. The infrared rays are then focused onto the infrared detector 138 which converts them into an electrical signal. The output from the infrared detector 138 is divided by the arithmetic unit 150 into an output indicative of the infrared ray of the wavelength $\lambda R$ and an output indicative of the infrared ray of the wavelength $\lambda M$. The arithmetic unit 50 then performs an arithmetic operation on these outputs to produce their logarithmic ratio, based on which the display 152 digitally displays the thickness of the film. To measure a profile of the film tube 116, the photodetector 132 of the infrared film thickness gage as shown is movable along a rail 154 extending concentrically around the film tube 116, with infrared radiation source 130 being positioned centrally in the film tube, as shown in FIG. 13. The film tube 116 is measured for thicknesses of its portions while the photodetector 132 makes one rotation or one cycle of scanning around the film tube 116 along the rail 154. The measurement accuracy is dependent on scanning errors made upon revolution of the photodetector 132, and hence it is important to reduce such scanning errors.

Tungsten-filament lamps have been used as the infrared source, but the directional distribution of radiation intensity of these lamps is not uniform upon scanning, the zero point shifts. Since the error introduced exceeds the required accuracy for such measurement, thickness gages using tungsten lamps are practically useless for measuring films during the inflation process.

The present invention in the above context will now be described in detail with reference to the accompanying drawings FIGS. 14 through 25 in which preferred embodiments of infrared film thickness gages are shown by way of example.

Figure 14:
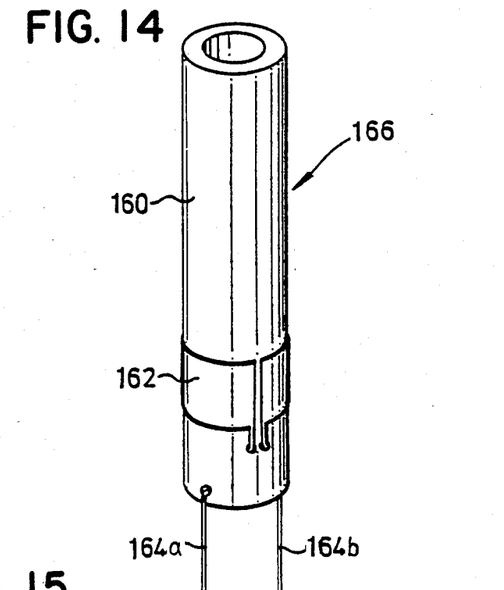
FIG. 14 is a perspective view of a source of infrared radiation according to an embodiment used in the present invention.

FIG. 14 shows a source of infrared radiation 166 according to an embodiment of the present invention. As shown, the infrared radiation source comprises a pipe 160 of ceramic material and a sheet-shaped heater 162 wound circumferentially around a portion of the ceramics pipe 164a, 164b connectable to a suitable power supply.

Figure 15:
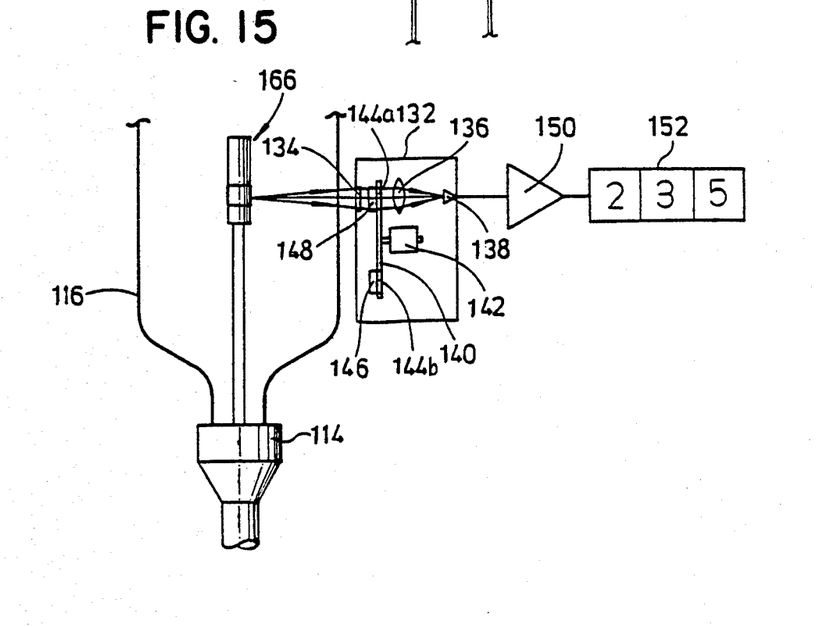
FIG. 15 is a schematic view of an infrared film thickness gage using the infrared radiation source as illustrated in FIG. 14.

As shown in FIG. 15, the infrared radiation source 166 composed of such a ceramic heater can be used in place of the conventional infrared radiation source 130 of FIG. 12. More specifically, an infrared film thickness gage according to the embodiment of FIG. 15 is substantially the same in construction as the infrared film thickness gage of FIG. 12 except for the type of infrared radiation source 166. Identical parts in FIG. 15 are denoted by identical reference numerals shown in FIG. 12. Accordingly, no additional detailed description of the thickness gage shown in FIG. 15 will be given.

Figure 16:
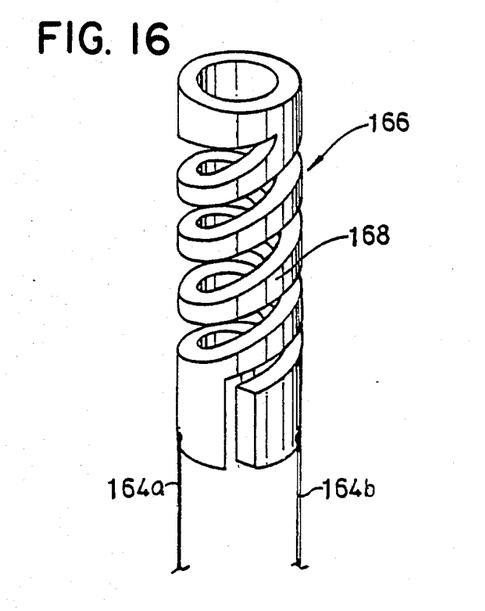
FIG. 16 is a perspective view of a source of infrared radiation according to another embodiment used in the present invention.
Figure 17:
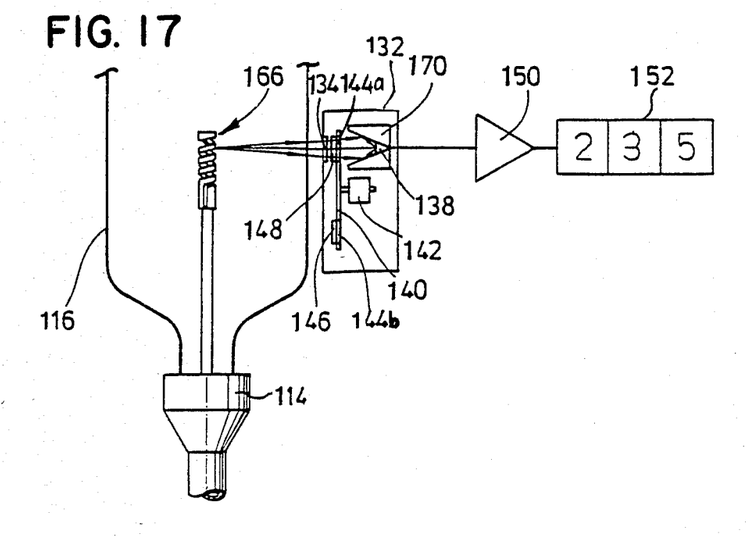
FIG. 17 is a schematic view of an infrared film thickness gage in which the infrared radiation source of FIG. 16 is used.
Figure 18:
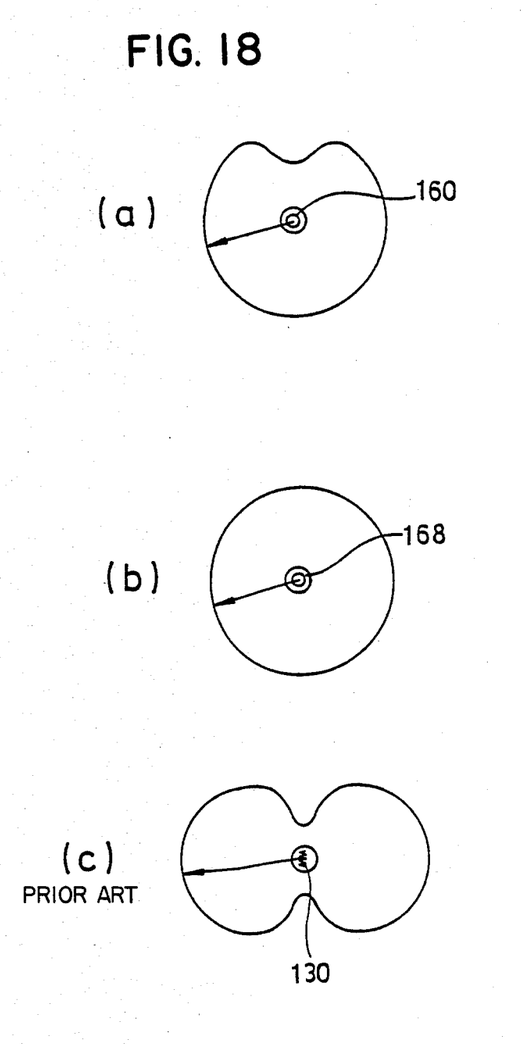

FIG. 16 illustrates an infrared radiation source 166 according to another embodiment of the invention. The infrared radiation source 166 includes a helical element 168 of SiC to which a pair of power supply lead wires 164a, 164b is connected. FIG. 17 shows an infrared film thickness gage which includes the infrared radiation source 166 composed of the helical SiC heater. The infrared film thickness gage shown in FIG. 17 includes a photodetector 132 having a conical light concentration guide 170 rather than the lens 136 as shown in FIG. 12. The other structures of the infrared film thickness gage of FIG. 17 are the same as those of the thickness gage shown in FIG. 15, and will therefore not be described in detail. Identical parts shown in FIG. 17 are denoted by identical reference numerals shown in FIG. 15.

The directional distribution characteristics of infrared radiation intensity of the ceramic heater (FIG. 14) and the helical SiC heater (FIG. 16) according to the present invention were measured by an infrared power meter and compared with the directional distribution characteristics of a conventional tungsten-filament lamp. These characteristics are shown in FIGS. 18(a), 18(b) and 18(c). A review of the directional distribution patterns shows that the directional distribution characteristics of radiation intensity of the infrared radiation sources used in the present invention, as shown in FIGS. 18(a) and 18(b), are substantially more uniform than the directional distribution characteristics of radiation intensity of the prior tungsten-filament lamp illustrated in FIG. 18(c). It has also been found that the helical SiC heater has a more uniform directional distribution of radiation intensity than the ceramic heater, as seen from a comparison between FIGS. 18(a) and 18(b). The above measurement results show that the infrared film thickness gages according to the invention have infrared radiation sources which have uniform directional distribution characteristics of radiation intensity. Therefore, any shift in the zero point upon scanning is much smaller than the zero point shifts obtained using the conventional infrared film thickness gage which relies on the tungsten-filament lamp.

Figure 19:
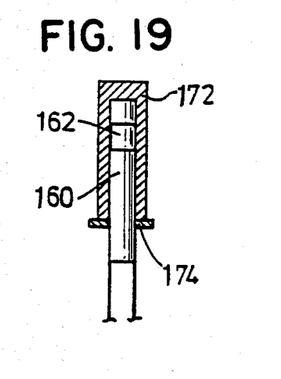
FIG. 19 is an elevational view, in partial cross section, of a modification of the infrared radiation source shown in FIG. 14.
Figure 20:
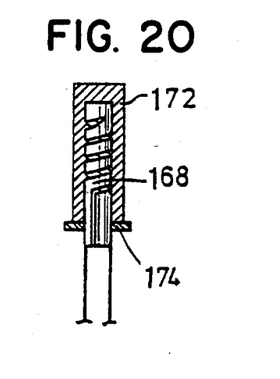
FIG. 20 is an elevational view, partly in cross section, of a modification of the infrared radiation source illustrated in FIG. 16.

FIGS. 19 and 20 show modifications respectively of the infrared radiation sources illustrated in FIGS. 14 and 16. In FIG. 19, the ceramic heater is covered with a quartz tube 172 which has one end closed off and has its surface sandblasted to provide a relatively rough finish. The quartz tube 172 is fixed to the ceramic pipe 60 by a fastener 174. As shown in FIG. 20, the helical SiC heater of FIG. 16 is covered with a quartz tube 172 of the same construction as that of the quartz tube shown in FIG. 19, with the quartz tube 172 being secured to the heater by a fastener 174. Since the heaters covered by the quartz tube 172 have a roughly finished surface, the infrared rays radiated from the infrared source are scattered by the rough surface of the quartz tube 172, resulting in more uniform directional distribution of radiation intensity. Since the quartz tube 172 prevents ambient air from directly contacting the heater, the heater temperature will not be lowered by air cooling, and the intensity of radiation from the infrared source can be more stabilized.

Figure 21:
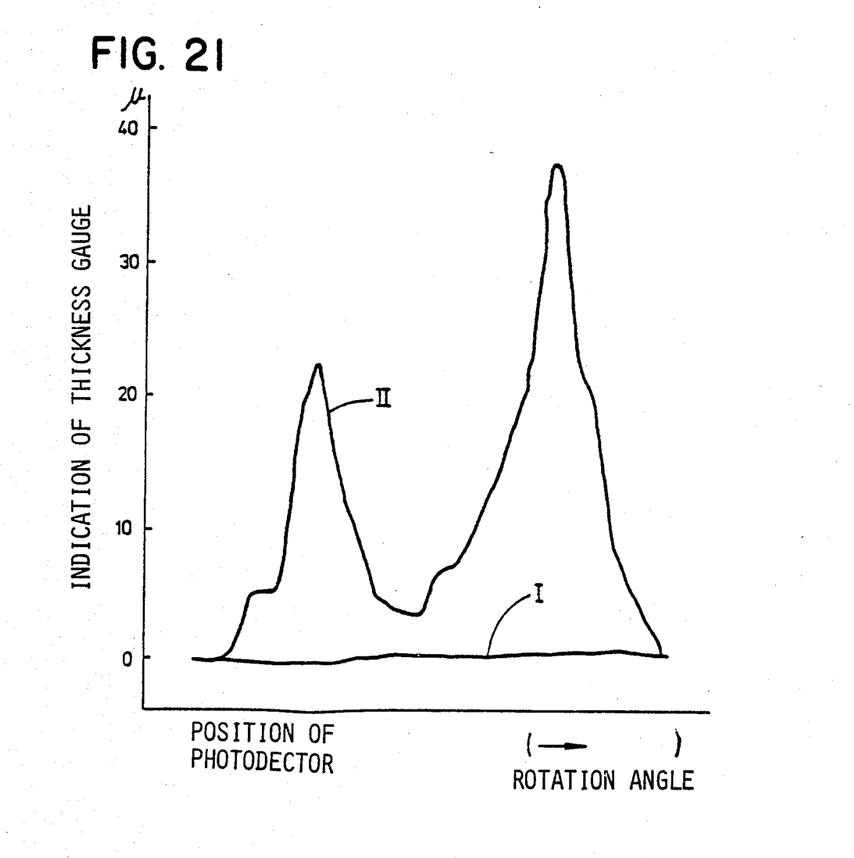
FIG. 21 is a graph showing for comparison curves of zero point shifting obtained from scanning with an infrared radiation source according to the invention and with a known infrared radiation source.

FIG. 21 shows characteristic curves showing zero point shifting upon scanning of an infrared film thickness gage using a helical SiC heater according to the present invention, and zero point shifting upon scanning of an infrared film thickness gage in which a known tungsten-filament lamp is employed. A study of FIG. 21 indicates that the helical SiC heater (curve I) is subjected to much fewer scanning errors than the tungsten-filament lamp (curve II), and can well meet the requirement of the measurement precision of $\pm 1\mu$ for thickness gages for inflated film tubes.

Figure 22:
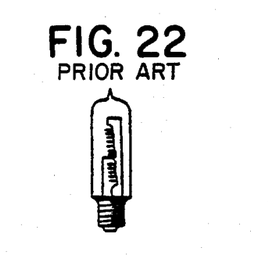
FIGS. 22 through 24 are perspective views of infrared radiation sources compared with an infrared radiation source according to the present invention.
Figure 23:
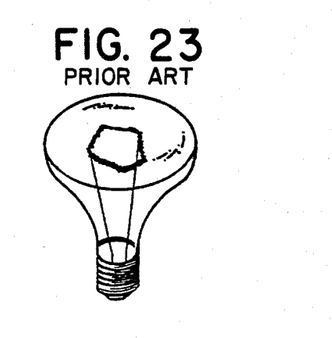
Figure 24:
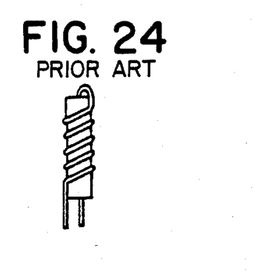
Figure 25:
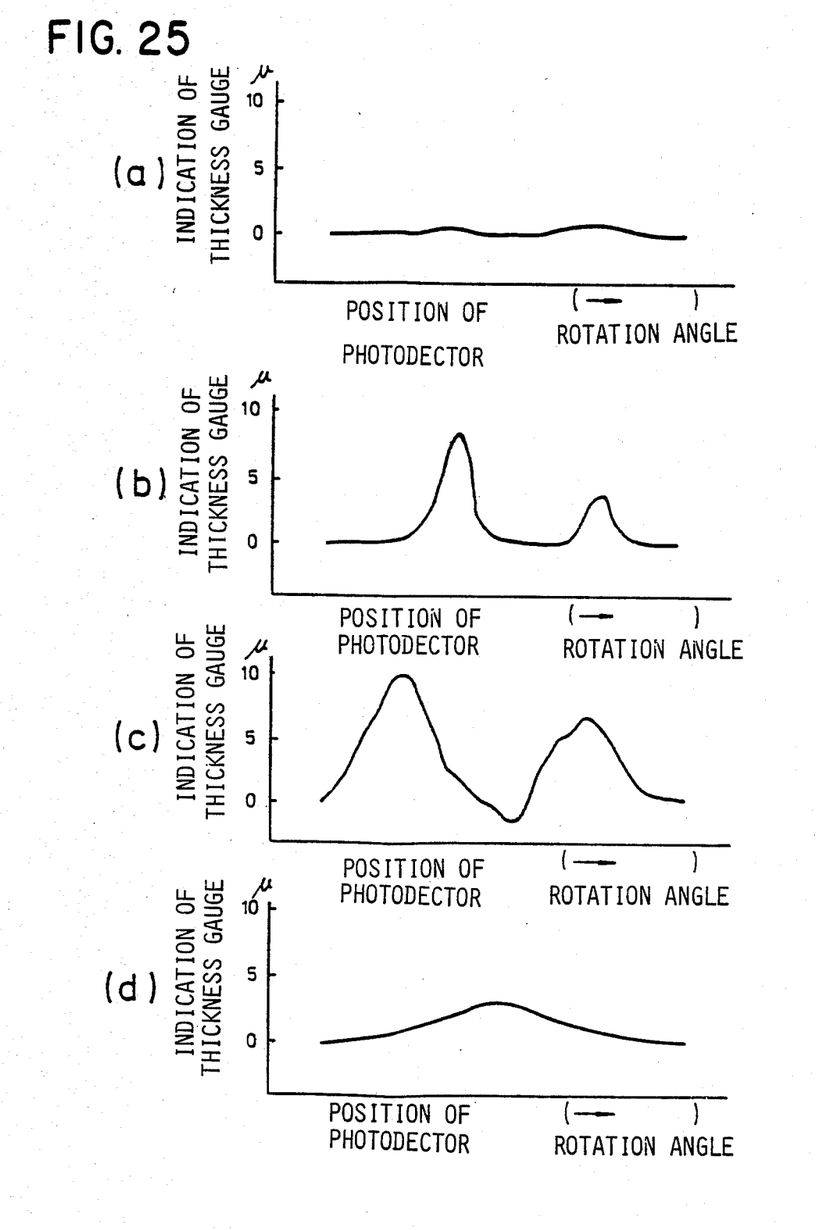

A ceramics heater according to the present invention was also measured for zero point shifting upon scanning for comparison with a halogen lamp as shown in FIG. 22, a tungsten-filament lamp having a pentagonal filament as shown in FIG. 23, and a heater of Nichrome as shown in FIG. 24. The results are shown in FIGS. 25(a), 25(b), 25(c), and 25(d). As is apparent from these graphs, it has been confirmed that the halogen lamp (FIG. 25(b)), the tungsten-filament lamp with the pentagonal filament (FIG. 25(c)), and the Nichrome heater (FIG. 25(d)) cause $\pm 1\mu$ or more of zero point shifting upon scanning, and hence are unsuitable for use as an infrared radiation source in the thickness gage for inflated films.

With the present invention, as described above with reference to the foregoing embodiments, scanning errors can be reduced to $\pm 1\mu$ or smaller by using a helical SiC heater or a ceramics heater as an infrared radiation source, which heater has uniform directional distribution of radiation intensity. Therefore, such a heater makes it practically feasible to build an infrared film thickness gage for measuring inflated films.

The infrared film thickness gage constructed as above according to the present invention is not limited to use as a thickness gage for inflated film tubes, but is also applicable to an apparatus in which a source of infrared radiation is disposed within a tubular material to be measured, and a photodetector is located outside of the tubular material, for measuring a physical quantity of the tubular material based on the intensity of infrared radiation having passed through the test material. The thickness gage of the invention has wide applicability to an apparatus having a photodetector that can be moved around an outer circumferential surface of a test material for scanning thereof to thereby measure physical quantities of parts of the test material.

While the present invention has been described with reference to the preferred embodiments, the present invention should not be interpreted as being limited to the illustrated embodiments, but many changes and modifications may be made within the spirit of the present invention.

I claim:

1. An infrared film thickness gage for measuring the thickness of film in a generally tubular shape during production by a film blowing process comprising a source of infrared radiation for irradiating a test film with infrared rays, a photodetector for receiving the infrared rays of reference and measurement wavelengths after the infrared rays have passed through the test film alternately, and means for converting an intensity of the received infrared rays into an electrical signal and for converting the electrical signal into an indication signal indicating film thickness, the source of infrared radiation comprising a radiating element supported only at one location and having electrical conductors attached only at the supported location to provide uniform directional distribution characteristics of radiation intensity over 360° from a region spaced from the support location and concentrically positioned in a film tube, and wherein said photodetector is positioned outside of said film tube in confronting relation to said source of infrared radiation, whereby the error in measuring the thickness of the film is no greater than about 1 $\mu$m.

2. The infrared film thickness gage according to claim 1, wherein said source of infrared radiation comprises a generally rod-shaped heater having a pipe of ceramic material and a generally sheet-shaped heater wound generally circumferentially around said pipe.

3. The infrared film thickness gage according to claim 1, wherein said source of infrared radiation comprises a generally helical-shaped heater of SiC.

4. The infrared film thickness gage according to claim 1, wherein the source of infrared radiation is enclosed in a tube having a relatively rough surface finish to scatter infrared rays and enhance the uniformity of the directional distribution characteristics.

5. The infrared film thickness gage according to claim 4, wherein the tube is made of quartz material.

6. The infrared film thickness gage according to claim 1, wherein an infrared long-pass filter having a cutoff wavelength in the vicinity of said reference and measurement wavelengths is positioned in the optical path of the photodetector, and wherein said infrared long-pass filter has an infrared transmittance which is held at a maximum in the vicinity of peaks of said reference and measurement wavelengths.

7. The infrared film thickness gage according to claim 6, wherein said infrared ray detector comprises a photoconductive detector having a thin photosensitive film of lead sulfide.

8. The infrared film thickness gage according to claim 6, wherein the infrared long-pass filter has a cutoff wavelength $\lambda c$ of $1.7\mu$.

9. The infrared film thickness gage according to claim 6, wherein the infrared long-pass filter has a cutoff wavelength $\lambda c$ of $1.4\mu$.

* * * * *